United States Patent
Hampp et al.

(10) Patent No.: US 6,927,050 B1
(45) Date of Patent: Aug. 9, 2005

(54) LINKER-FREE COVALENT COUPLING OF BACTERIORHODOPSIN IN PURPLE MEMBRANE FORM

(75) Inventors: Norbert Hampp, Schillerstasse 10, D-35287 Amöneburg-Rossdorf (DE); Ame Seitz, Marburg (DE); Ralf Paster-Nack, Griesheim (DE); Hans-Lothar Fuchsbauer, Mühltal/Traisa (DE)

(73) Assignee: Norbert Hampp, Amoneburg-Rossdorf (DE)

(*) Notice: Subject to any disclaimer, the term of this patent is extended or adjusted under 35 U.S.C. 154(b) by 0 days.

(21) Appl. No.: 09/937,754

(22) PCT Filed: Mar. 31, 2000

(86) PCT No.: PCT/EP00/02904
§ 371 (c)(1),
(2), (4) Date: Jan. 8, 2002

(87) PCT Pub. No.: WO00/58450
PCT Pub. Date: Oct. 5, 2000

(30) Foreign Application Priority Data

Mar. 31, 1999 (DE) .......................................... 199 14 702
Nov. 8, 1999 (DE) .......................................... 199 53 607

(51) Int. Cl.⁷ ........................... C12N 11/00; C12N 9/10; C07K 17/00
(52) U.S. Cl. ........................ 435/174; 435/193; 530/350
(58) Field of Search ................................ 435/174, 193; 530/350

(56) References Cited

U.S. PATENT DOCUMENTS 5,922,843 A    7/1999 Tan et al.
6,140,012 A * 10/2000 Smithey et al. ......... 430/270.14
6,472,182 B1 * 10/2002 Kobayashi et al. ........ 435/71.1
6,616,964 B1 *  9/2003 Hampp et al. .................. 427/7

FOREIGN PATENT DOCUMENTS

EP    0 417 541 A    3/1991
EP    0 532 029 A    3/1993
EP    0 726 317 A    8/1996
WO      99/06446 A    2/1999

OTHER PUBLICATIONS

Lehninger, A. Biochemistry (1975) (Worth, publishers: NY) p. 196–197.*
Dutton et al. "Crosslinking and Labeling of Membrane Protein by Transglutaminase–Catalyzed Reaction" Proc. Nat. Acad. Sci. (1975) 72(7): 2568–71.*
McDowell et al. "Transglutaminase Modification of Rhodopsin in Retinal Rod Outer Segment Dick Membranes" Arch. Biochem. Biophys. (1986) 249(2): 506–514.*
Gaffney, B.J., "Chemical and biochemical crosslinking of membrane components", 1985, Biochimica Biophysica Acta, vol. 822, pp. 289–317.
Singh, A.K. et al., "Photoactive bacteriorhodopsin variants", 1997, Radiation Physics and Chemistry, vol. 49, No. 1, pp. 131–134.
Brauchle, C. et al, "Optical Applications of Bacteriorhodopsin and Its Mutated Variants", 1991, Advanced Materials, vol. 3, No. 9, pp. 420–428.
Braeuchle, C. et al, "Optical Information Processing with Bacteriorhodopsin and Its Genetically Modified Variants", 1993, Proceedings of the Quantum Electronics and Laser Science Conference, Conf. 4, p. 2.

* cited by examiner

Primary Examiner—Jean C. Witz
Assistant Examiner—Susan Hanley
(74) Attorney, Agent, or Firm—Sutherland Asbill & Brennan LLP (57) ABSTRACT

A process is described for the linker-free covalent coupling of bacteriorhodopsin in a purple membrane form.

16 Claims, 7 Drawing Sheets

Lys A)
Gln B)
C)

LINKER-FREE COVALENT COUPLING OF BACTERIORHODOPSIN IN PURPLE MEMBRANE FORM

The invention concerns the linker-free covalent coupling of bacteriorhodopsin (BR) in a membrane-bound form, in particular in a purple membrane form.

Bacteriorhodopsin (BR) is a membrane protein which for example occurs in halobacteria in the form of a two-dimensional, disk-shaped, water insoluble crystal, the so-called purple membrane (PM). The purple membrane has a thickness of ca. 5 nm. The diameter of the purple membrane is typically in the range of 300 nm to 1000 nm.

The purple membrane is composed of α-helical bacteriorhodopsin molecules and ca. 10 lipid molecules per bacteriorhodopsin molecule. The bacteriorhodopsin is almost completely embedded in the lipid membrane formed from lipid molecules. This results in an exceptional thermodynamic stability.

Bacteriorhodopsin in the purple membrane form is used technically as a photochromic material for optical applications. In addition bacteriorhodopsin in the purple membrane form is technically important as a material with photoelectric properties.

Covalent cross-linking between purple membranes is advantageous for these technical applications. In photovoltaic applications of bacteriorhodopsin about 300 mV is obtained per purple membrane layer. Elements which yield higher voltages can be obtained by forming several purple membrane layers on top of one another by means of covalent cross-linking. Another interesting aspect is the covalent coupling of purple membranes to surfaces, polymers or smaller molecules e.g. dyes.

Usually one tries to use low-molecular linker molecules such as glutaraldehyde for the covalent binding of purple membranes. However, these coupling reactions result in a very poor yield. The reason for this is that only a few amino acids of bacteriorhodopsin are present outside the lipid double layer of the membrane, are sterically hindered and hardly react with the low-molecular coupling reagents. However, low-molecular coupling reagents have a further serious disadvantage. They can penetrate through the proton channel into the active centre of bacteriorhodopsin. In particular a reaction of the linker molecules with the binding site of the retinal aldehyde at lysine-216 (Schiff base) results in irreversible damage to the desired functions of the protein. Hence the widely used low-molecular coupling reagents that react with amino groups are particularly disadvantageous. Furthermore, the low-molecular linkers have to be added in excess in order to at least achieve a reasonably acceptable yield and cross-linking rate. Numerous non-reacted molecules remain in the material and have to be removed after the reaction. This is for example not possible in the manufacture of optical films.

The disadvantages of low-molecular linkers are summarized in the following:

Few amino acids of bacteriorhodopsin are accessible to linkers.
Linkers that react with functional amino groups should not be used.
Non-reacted linkers have to be removed since otherwise an uncontrolled after-reaction of long duration would occur which would lead to a continuous change in the material properties and a lack of long-term stability.

Hence an object of the invention was to provide a process for the covalent linkage of bacteriorhodopsin in a membrane form and in particular for the direct cross-linking of purple membranes without using low-molecular linkers. A further field of application is the coupling of bacteriorhodopsin in a membrane form to surfaces, polymers or auxiliary substances, in particular dyes.

This object is achieved by a process for the production of covalently cross-linked bacteriorhodopsin which is characterized in that bacteriorhodopsin is covalently cross-linked in a membrane-bound form as a substrate of a transglutaminase and in particular of a bacterial transglutaminase.

The term bacteriorhodopsin as used herein is understood to include the bacteriorhodopsin wild-type (BR-WT) as well as bacteriorhodopsin variants. The term bacteriorhodopsin variants includes bacteriorhodopsin molecules which differ from BR-WT by the addition, substitution, deletion and/or insertion of amino acids and in particular of at least one, particularly preferably of at least two and most preferably at least three and up to 50, preferably up to 20 and particularly preferably up to 10 amino acids. The term variants additionally includes bacteriorhodopsin molecules in which retinal is replaced by retinal-like molecules and bacteriorhodopsin molecules that have been chemically modified for example by introducing protecting groups or functional side groups.

For the purposes of this invention the term bacteriorhodopsin also encompasses membrane proteins that are structurally related to bacteriorhodopsin, that are present in a membrane-bound form and have a homology of at least 70%, more preferably of at least 80% and most preferably of at least 90% to the bacteriorhodopsin wild-type. Homology as used herein is defined as $$H (\%)=(1-A/[BR\text{-}WT])\times 100,$$

in which H denotes the homology in percent, A represents the number of changes present compared to the bacteriorhodopsin wild-type sequence and [BR-WT] is the number of amino acids in the bacteriorhodopsin wild-type sequence.

Examples of membrane proteins in a membrane-bound form that are structurally related to bacteriorhodopsin and are comprised by the invention are halorhodopsin and sensorrhodopsin. These membrane proteins are present in a non-crystalline membrane form.

Bacteriorhodopsin materials that are preferably used according to the invention comprise the bacteriorhodopsin wild-type and the bacteriorhodopsin variants with a modified amino acid sequence. The bacteriorhodopsin variants preferably have a modified physical function and in particular a modified light sensitivity, a modified colour or modified kinetics of the photochromic properties of bacteriorhodopsin. Bacteriorhodopsin variants are most preferred in which binding sites for enzymatic cross-linking with transglutaminase have been specifically deleted or introduced. Bacteriorhodopsin variants are particularly preferably used in which Gln or Lys have been deleted or substituted by other amino acids. In bacteriorhodopsin a Lys binding site is located intracellularly (=C-terminus) at positions Lys41, Lys42, Lys159 and Lys172 and extracellularly (N-terminus) at position Lys129. Gln binding sites are located in bacteriorhodopsin extracellularly (=N-terminus) at positions Gln3 and Gln75. It was found that especially amino acids Gln3 and Lys129 act as binding sites in the reaction with transglutaminase.

Bacteriorhodopsin variants are also preferred in which Gln or Lys is introduced into a loop in such a manner that it is accessible to transglutaminase. Those bacteriorhodopsin variants are particularly preferred in which one or two binding sites for transglutaminase are present. If, two binding sites are present which are accessible to transglutaminase, the two binding sites can either be arranged on the same side of the membrane or preferably on different sides of the membrane i.e. one binding site is on the cytoplasmic side and one is on the extracellular side. This enables an oriented overlayering of membranes rather than a statistical cross-linking. Oriented overlayering enables the generation of elements in which the voltage of 300 mV per layer increases with the number of layers. In previously known processes for the formation of multilayer BR purple membranes a preferred orientation of only about 10% is obtained. In contrast the invention enables an oriented overlayering having a considerably higher preferred orientation. Preferably about 4 to 10 BR purple membrane layers are stacked on top of one another enabling a preferred orientation of more than 30%, preferably of more than 50% and particularly preferably of more than 80% to be obtained.

Furthermore bacteriorhodopsin variants are preferred in which retinal is replaced by retinal-like molecules which for example enables changes to be made in the photocycle of the bacteriorhodopsin material. Retinal-like molecules are molecules which can be incorporated as a chromophore into bacteriorhodopsin and differ from retinal for example by a derivatization.

Another preferred class of bacteriorhodopsin materials are bacteriorhodopsin variants or bacteriorhodopsin wild-type which have been chemically modified. Suitable modifications are described for example in the U.S. Pat. No. 5,922,843. The variants can also be modified by blocking amino acids for example by means of protecting groups or other chemical modifications of the amino acid side chains.

Bacteriorhodopsin variants can also be obtained by enzymatic pretreatment of the bacteriorhodopsin wild-type or bacteriorhodopsin variants. An enzymatic cleavage can for example be carried out using peptidases in particular to remove the amino terminus or to cleave the loops located outside the membrane.

Variants can also be used which have a combination of several of the above-mentioned modifications.

It surprisingly turned out that bacteriorhodopsin in a membrane-bound form and in particular in a purple membrane form is a substrate of transglutaminase and in particular of bacterial transglutaminase (bTGA). This is unexpected especially because, as elucidated above, the amino acids of bacteriorhodopsin in the membrane form and in particular in the purple membrane form are mainly located within the lipid double layer of the membrane and are thus inaccessible. Bacteriorhodopsin is not in a free form in the purple membrane form but rather is present as a disk-shaped protein-lipid crystal structure of higher order. Nevertheless it is surprisingly accepted and converted as a substrate by bacterial transglutaminase.

Previously it was only known that transglutaminase could catalyse the coupling of soluble proteins such as enzymes to a carrier such as gelatin or to a marker enzyme. Such a process is described for example in DE 197 32 917 C1. For this purpose protein solutions are reacted with transglutaminase. No indication is disclosed in DE 197 32 917 that water-insoluble proteins or even water-insoluble protein-lipid aggregates are accepted as substrates by transglutaminase. Even less consideration is given to bacteriorhodopsin or even bacteriorhodopsin in a purple membrane form.

A similar process for reacting water-soluble proteins with TGA such as the cross-linking of casein or gelatin is also described in U.S. Pat. No. 5,731,183 and EU 5,948,662. For this purpose solutions of the proteins are reacted with the special transglutaminases disclosed in these US patents. There is no disclosure or indication that also water-insoluble proteins or even structures of a higher order could serve as a substrate for TGA. Even less mention is made of bacteriorhodopsin or even bacteriorhodopsin in a purple membrane form.

It was now surprisingly found that it is possible to use TGA to directly cross-link bacteriorhodopsin in the membrane form and even in the purple membrane form without addition of low-molecular linker molecules. Furthermore polymers and other substances such as surfaces or auxiliary substances e.g. dyes can also be bound to the bacteriorhodopsin. Cross-linking takes place at about 40° C. Subsequent heating the reaction mixture to 80° C. inactivates the TGA. Bacteriorhodopsin in the purple membrane form survives the heat treatment without damage. Thus the reaction can be specifically stopped. A removal of excess low-molecular linkers is not necessary.

Bacteriorhodopsin purple membranes and in particular different variants of bacteriorhodopsin purple membranes can act as a first as well as a second substrate for TGA and in particular for bTGA. This results in numerous possibilities for directly cross-linking purple membranes to one another or/and to covalently couple polymers, surfaces or/and substrates to bacteriorhodopsin in a purple membrane form in a cross-linked as well as in a non-cross-linked form.

Hence one aspect of the invention concerns a process for covalently linking bacteriorhodopsin in a membrane form and in particular in a purple membrane form to polymers, surfaces or/and auxiliary substances by means of TGA in which the bacteriorhodopsin and the other substrate is reacted with a transglutaminase and covalently cross-linked together. Such a process can for example be used to form covalently linked conjugates composed of bacteriorhodopsin in the purple membrane form and another molecule. Suitable polymers that can be covalently bound to the bacteriorhodopsin in a purple membrane form by means of TGA comprise for example gelatin, polyvinyl alcohol and polyethylene whose side groups may be modified. Suitable substrates or auxiliary substances are in particular low-molecular compounds such as dyes.

Since no linker molecules at all are required according to the invention, this results in considerable economic and technological advantages.

In addition to the bacteriorhodopsins in a membrane-bound form described above, it is also possible according to the invention to covalently cross-link bacteriorhodopsin in a soluble form and in particular in a monomeric or trimeric form using a transglutaminase. In particular according to the process of the invention bacteriorhodopsin like that which is formed by the heterologous expression of bacteriorhodopsin or bacteriorhodopsin like that which is formed by the solubilization of purple membranes (monomerized bacteriorhodopsin) can be reacted as a substrate of a glutaminase and covalently cross-linked.

Furthermore according to the invention it is also possible to react membrane proteins that are different from bacteriorhodopsin as a substrate of a transglutaminase and hence covalently cross-link them provided they are in a membrane-bound form. In particular membrane proteins which contain several and in particular four to eight helical (above all α-helical) membrane-spanning amino acid sections can be reacted. Examples of suitable membrane proteins are channel proteins, porters, receptors, G-proteins etc.

The process according to the invention can be used in particular to covalently cross-link two identical or different bacteriorhodopsin materials as was described above. In a further preferred embodiment the process according to the invention is used to covalently bind a bacteriorhodopsin material to another material. A preferred example of this is the covalent binding of bacteriorhodopsin materials and in particular bacteriorhodopsin in a purple membrane form to a surface, to a polymer or/and to a low-molecular compound (also referred to herein as auxiliary substance).

For the covalent binding to a surface the bacteriorhodopsin is for example reacted as a substrate of transglutaminase using a molecule as a second substrate which, in addition to the binding group for the transglutaminase, has another functional group such as a terminal thiol group. The adduct formed by the reaction with transglutaminase can then be immobilized to a surface by means of the introduced functional group. Introduction of a thiol group for example enables the bacteriorhodopsin to be covalently immobilized on a gold surface. This enables an oriented immobilization of bacteriorhodopsin, in particular in the purple membrane form, since only the side of the bacteriorhodopsin on which the thiol group has been introduced can be covalently bound to the surface.

In addition it is also possible to use transglutaminase to directly covalently bind bacteriorhodopsin to surfaces provided the surface has groups which can act as a substrate for the transglutaminase.

In addition the process according to the invention enables bacteriorhodopsin to covalently bind to a polymer. In this case an oligomer or polymer which can be of natural or synthetic origin is linked with bacteriorhodopsin using the process according to the invention. An example of a natural polymer is gelatin, an example of a preferred synthetic polymer is polyvinyl alcohol. A prerequisite for a successful reaction is that the oligomer or polymer contains a side group which is a substrate of the transglutaminase i.e. contains a glutamine(Gln) or a lysine(Lys) residue or contains a glutamine analogue or a lysine analogue or a part of glutamine or a part of lysine which is recognized by transglutaminase as a substrate and in particular a part comprising at least three C atoms and an amino group.

Such a group can be already present in the polymer such as in gelatin or it can be chemically introduced.

A material is obtained by the process according to the invention in which bacteriorhodopsin, in particular in the purple membrane form, is present covalently coupled to a polymer in a stoichiometric manner. This has considerable advantages in the processing of a material. In particular there is no demixing which frequently occurs with polymers that are not soluble in one another and have only been physically mixed. In addition it enables materials containing bacteriorhodopsin to be processed in organic solvents when the bacteriorhodopsin is bound to an oligomer/polymer that is soluble in water or a buffer (for enzymatic cross-linking) as well as in organic solvents.

In a further preferred embodiment the bacteriorhodopsin is cross-linked with an oligomer/polymer which can in turn undergo further polymerization reactions or cross-linking reactions. Such further cross-linking or polymerization reactions can for example be initiated with UV light or by a radical starter. This enables the production of bulk materials which contain homogeneously dispersed bacteriorhodopsin. Such materials can be advantageously used to produce bacteriorhodopsin cubes such as those that can be used for three-dimensional data storage. Such materials have previously been prepared by adding bacteriorhodopsin during the polymerization of for example acrylic acid or acrylamide-based polymers in aqueous solvents, in which no cross-links are formed between the bacteriorhodopsin and the polymer. When the water is removed there is often a considerable shrinkage. In addition demixing phenomena are observed in such materials of the prior art which lead to an inhomogeneous distribution of the bacteriorhodopsin in the material.

In a further preferred embodiment the bacteriorhodopsin material is covalently bound to a low-molecular compound. The low-molecular compound is characterized in that it is a substrate of transglutaminase i.e. in particular a glutamine analogue or a lysine analogue. The low-molecular compound which is also referred herein as auxiliary substance can be selected from the group comprising dyes, fluorochromes, lipids, peptides, oligomeric and polymeric nucleic acids such as DNA/RNA/PNA etc., synthetic oligomers and polymers, proteins (avidin-biotin etc.), lectins, polysaccharides, conductive polymers and others. The process according to the invention enables a specific stoichiometric site-selective coupling of the compounds to bacteriorhodopsin and in particular to bacteriorhodopsin in a purple membrane form.

Dyes and fluorochromes are in particular covalently coupled in order to change the initial colour state of the bacteriorhodopsin or of the purple membrane. This has the advantage that no demixing occurs between bacteriorhodopsin and the dye or fluorochrome and that the processing is not adversely affected by different solubilities of the materials.

Lipids can be covalently coupled in order to anchor bacteriorhodopsin, in particular in a membrane form, to another lipid membrane in which case the other membrane is preferably also a purple membrane and particularly preferably also a bacteriorhodopsin purple membrane. Lipid-coupled bacteriorhodopsin materials can also be used advantageously for the Langmuir-Blodgett technique.

The coupling of bacteriorhodopsin to peptides enables the introduction of immunological tags and materials are obtained having a selective high-affinity binding capability (e.g. antigen-antibody interaction).

The coupling of bacteriorhodopsin to oligomers and in particular to oligomeric or polymeric nucleic acids such as DNA, RNA, PNA etc. enables the construction of three-dimensional oriented structures.

The covalent coupling of bacteriorhodopsin to synthetic oligomers or polymers enables cross-linked materials to be obtained which are stable towards demixing.

Materials having a high complex formation constant can be obtained by covalently coupling proteins such as avidin, biotin or such like which are in particular a partner of a selective, high-affinity binding pair.

Proton-conducting materials such as proton-conducting polymers or membranes can be preferably coupled to the bacteriorhodopsin as conductive materials.

A further subject matter of the present invention is a linker-free covalently cross-linked bacteriorhodopsin which can be obtained by the procedures described above. Such a material which can be exclusively composed of bacteriorhodopsin or of bacteriorhodopsin and other materials or substances covalently bound thereto, has structural differences compared to known bacteriorhodopsin materials which are very advantageous. In the direct coupling according to the invention there is no intermediate use of a linker and hence the bacteriorhodopsin materials are also directly bound in the material that is obtained and are not cross-linked via linkers. As a result the disadvantages associated with the use of linkers as described above can be eliminated. Moreover, in contrast to the physical mixtures known in the prior art, the covalent bonds used to couple bacteriorhodopsin to other materials enables, stable homogeneous materials to be obtained. Such materials are especially suitable for use in data storage. The oriented arrangement of several layers of BR purple membranes having a high preferred orientation enables materials to be obtained that exhibit improved properties in photoelectric applications as described for example by F. Hong, Progress in Surface Science 62 (1999), 1–237. Such materials generate higher voltages when illuminated than known less oriented BR materials and can be used in particular as switches or control elements.

The invention is further elucidated by the following examples and figures,

FIG. 1A shows bacteriorhodopsin wild-type (BR-WT), FIG. 1B shows the bacteriorhodopsin variant BR-D2N and FIG. 1C shows BR-WT and BR-D2N cross-linked together after 24 hours incubation with BTGase (bacterial transglutaminase).

FIG. 6 shows an example of a three-dimensional structure of bacteriorhodopsin purple membranes. An adhesive layer 7, e.g. nucleic acid oligomers, is applied to a surface or to a substrate 6. The purple membranes 8 are modified with functional groups in such a manner that the functional groups attached to the one side of the purple membrane can in each case interact with the functional groups attached to the other side of another purple membrane. For example the purple membrane is modified with nucleic acid oligomers in such a manner that the oligomers on both sides can hybridize with one another i.e. the extracellular purple membrane can hybridize with the cytoplasmic side of the purple membrane. This results in an oriented binding 9 of purple membrane to the substrate and in an oriented self organization of the purple membranes in the third dimension. A highly oriented anisotropic layer structure can be obtained in this manner. The photovoltages generated by the individual purple membrane forms now no longer compensate one another which would be the case for a random arrangement but rather they accumulate. In this manner it is possible to obtain elements having an adjustable photovoltage which is theoretically about 300 mV× number of layers.

Figure 7:
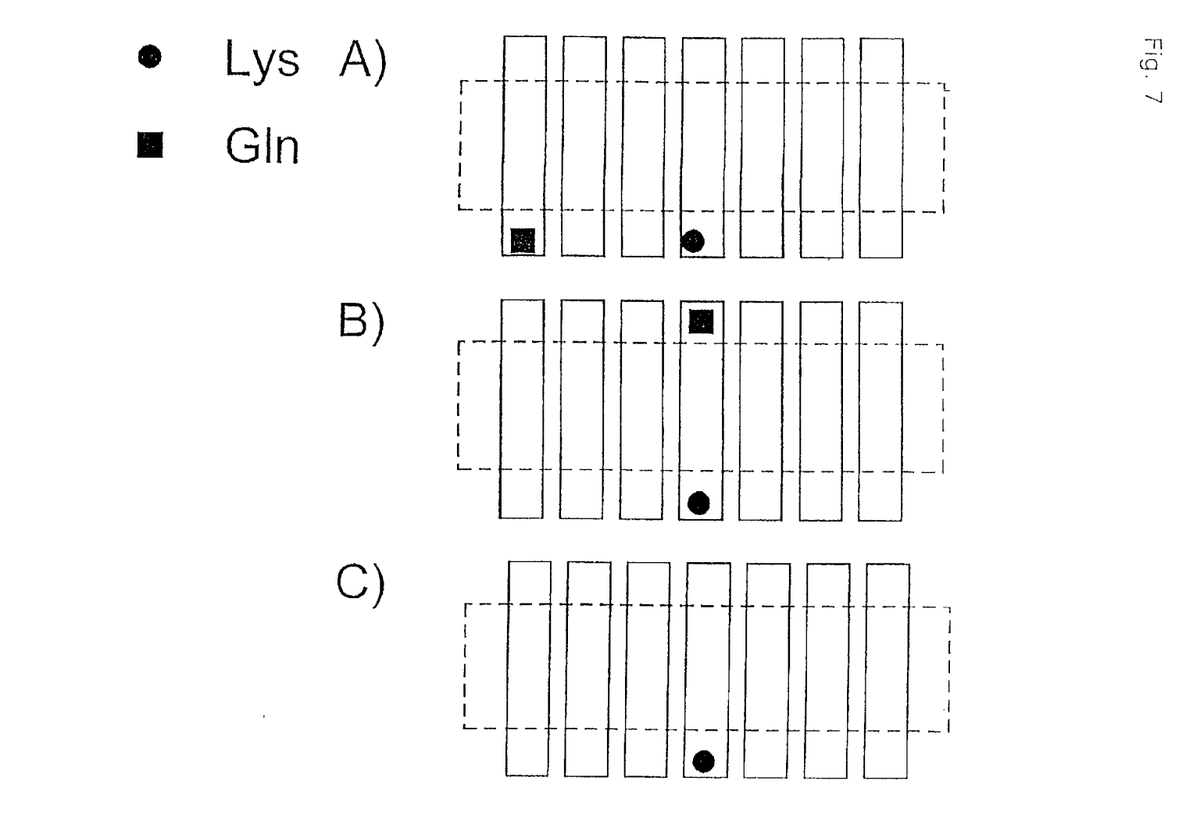
FIG. 7 shows purple membranes (dashed lines) with embedded bacteriorhodopsin amino acid columns (shown schematically as solid boxes). Lysine (Lys) and glutamine (Gln) that are accepted by transglutaminase (TGA) are shown as filled circles (Lys) or filled squares (Gln).

In the case of the wild-type bacteriorhodopsin the binding sites that are accessible to transglutaminase i.e. Gln3 and K129 are on the same side of the membrane (FIG. 7A). In a preferred embodiment a bacteriorhodopsin variant is used which has one binding site on the inside and one binding site on the outside of the membrane i.e. one binding site on the cytoplasmic side of the membrane and one binding site on the extracellular side of the membrane. Such a variant is preferably obtained by leaving Lys129 unchanged and deleting Gln3 and instead introducing a Gln in a loop on the other side of the membrane (FIG. 7B). In a further preferred embodiment a bacteriorhodopsin variant is used which has exactly one binding site (inside or outside) which can for example be obtained by removing the other possible binding sites (FIG. 7C).

EXAMPLE

Example 1

5 ml of a 42.5% and 37.5% sugar solution are used in order to generate a linear sugar gradient with a conventional gradient mixer. This gradient is used to analyse cross-linked and non-cross-linked bacteriorhodopsin.

Example 2

Figure 1:
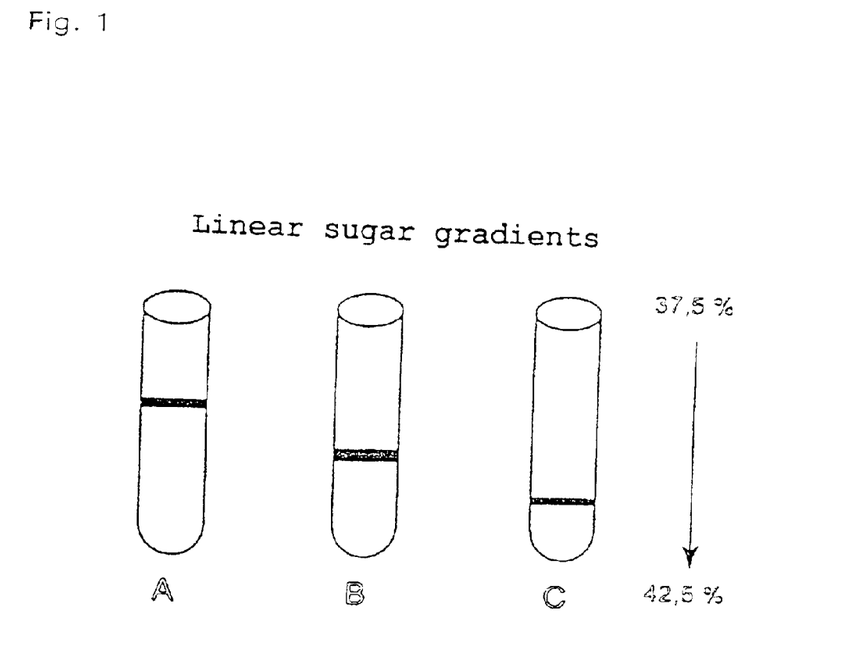
FIG. 1 being a schematic representation of the results of a sugar density gradient centrifugation.

A bacteriorhodopsin wild-type (WT) solution (20 mg/ml) and a solution of the bacteriorhodopsin variant BR-DZN (20 mg/ml) are mixed with buffer (pH 7.0, 100 mM phosphate buffer) and BTGase (9.3 U/ml) solution such that the BTGase is in a four-fold excess compared to bacteriorhodopsin. The incubation is carried out for 24 h at 40° C. Afterwards the reaction mixture contains virtually only cross-linked bacteriorhodopsin (FIG. 1C).

Example 3

Figure 2:
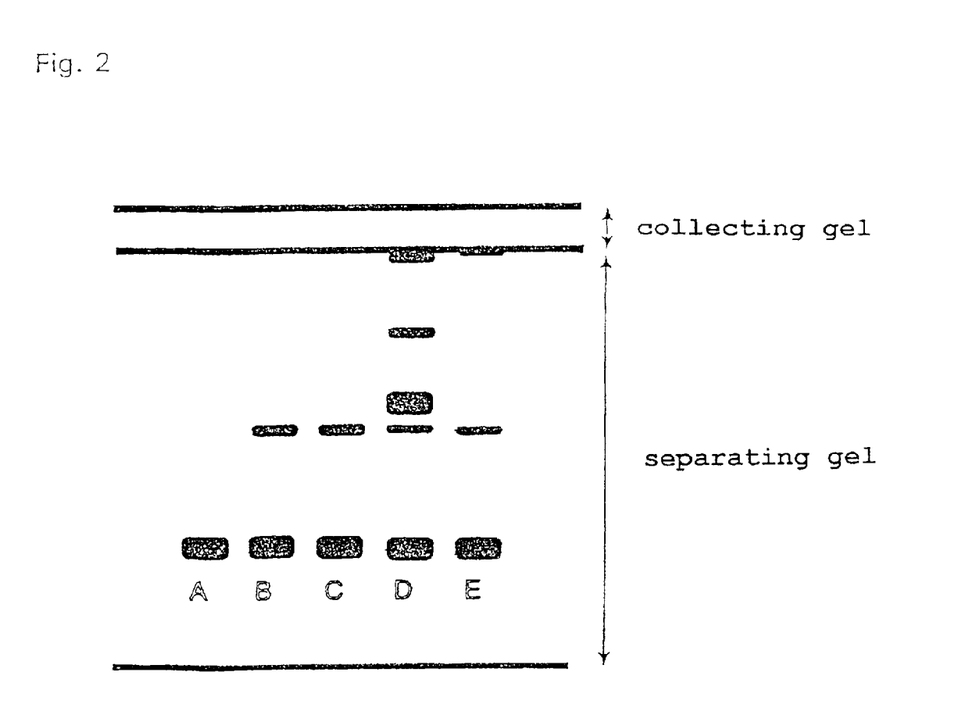
FIG. 2 shows a schematic representation of SDS-PAGE. A) BR-WT; B) BR-WT+BTGase, incubated for 0 hours at 37° C.; C) BR-WT+BTGase, incubated for 10 minutes at 37° C.:, D) BR-WT+BTGase, incubated for 20 minutes at 37° C.; E) BR-WT+BTGase, incubated for 120 minutes at 37° C.
Figure 3:
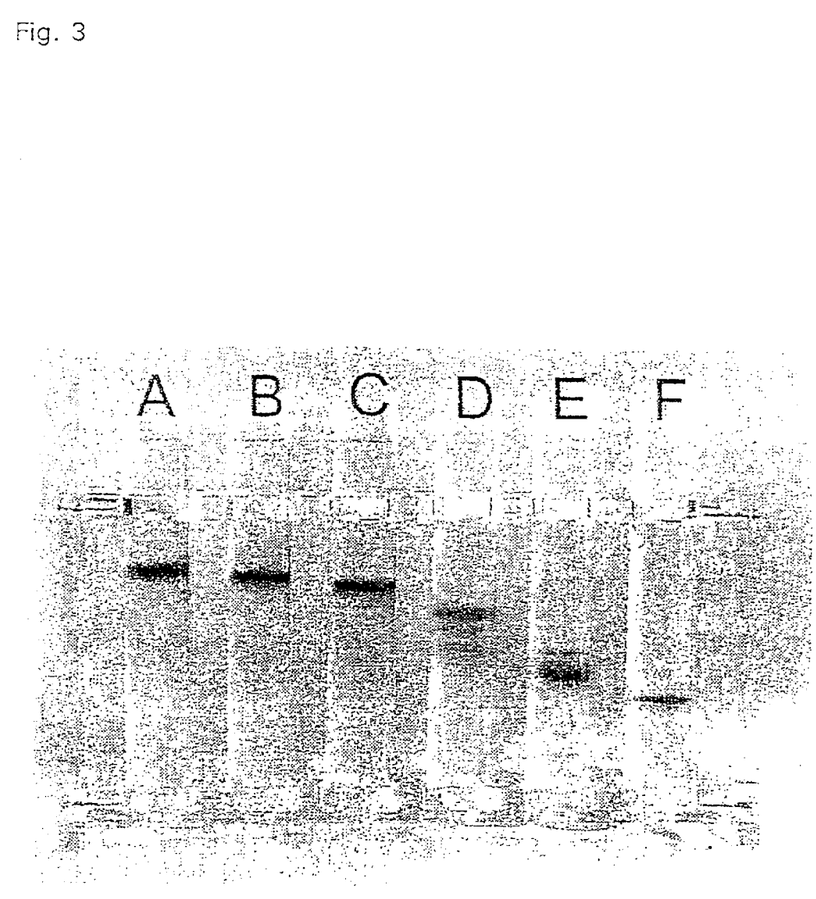
FIG. 3 shows the formation of cross-linked products of Lit BR-WT and BR-D2N in the presence of bacterial transglutaminase versus time.
Figure 4:
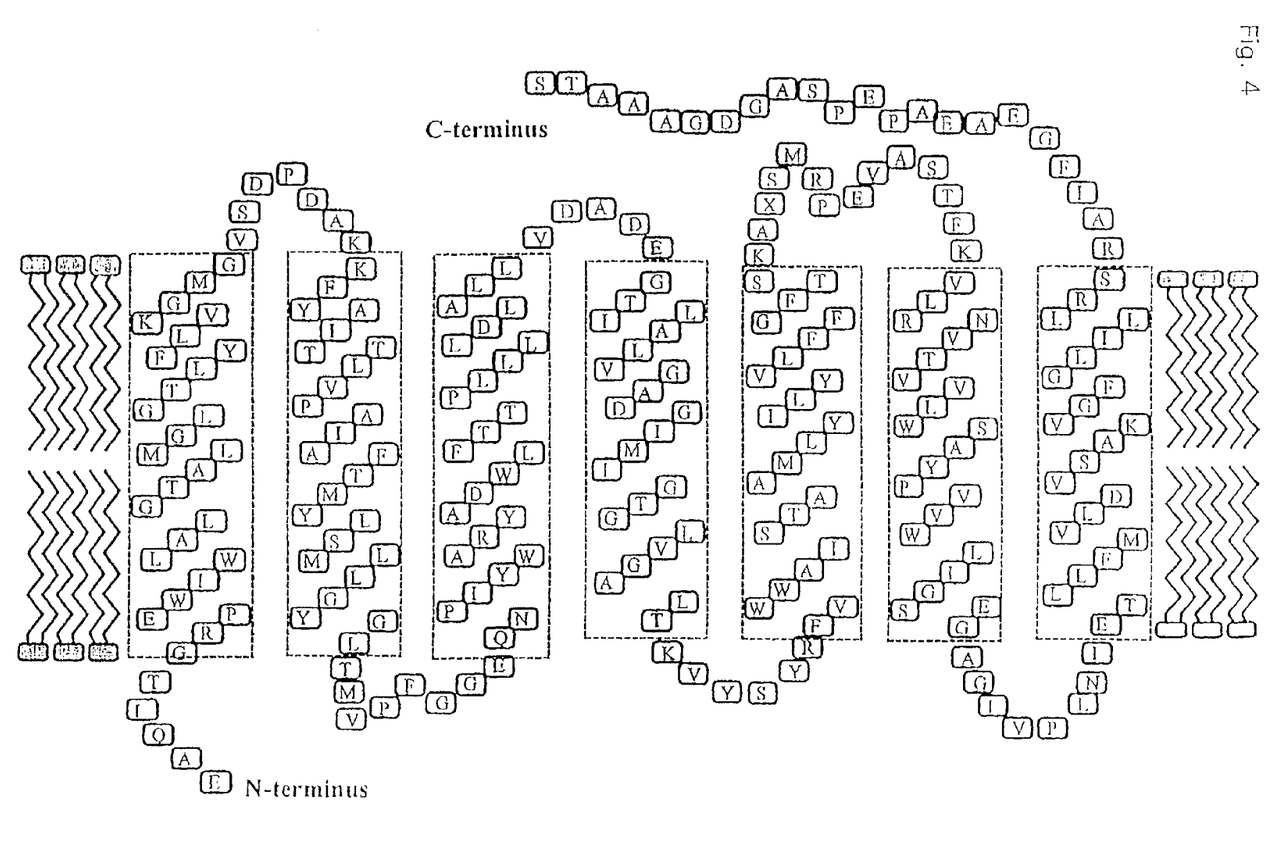
FIG. 4 shows the sequence of bacteriorhodopsin with the transmembrane arrangement modified according to R. R Birge, Photophysics and Molecular Electronic Applications of the Rhodopsins, Annu. Rev. Phys. Chem. 41 (1990), 683–733.
Figure 5:
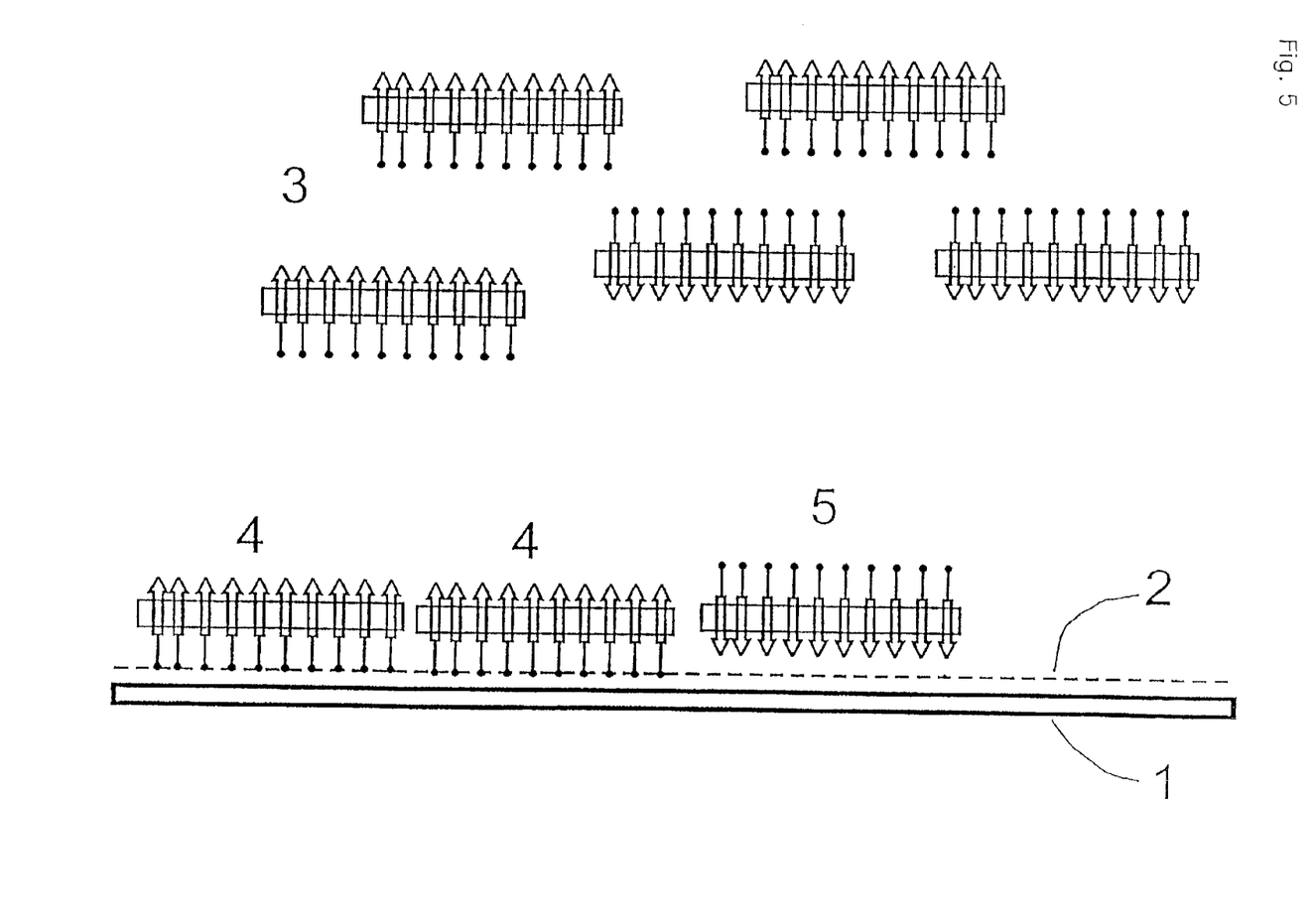
FIG. 5 shows an example for an oriented deposition of bacteriorhodopsin in a membrane form on surfaces. A layer 2 containing gold is applied to a wafer 1. This surface is contacted with bacteriorhodopsin purple membranes 3 suspended in a solvent which have been thiol-modified by a process according to the invention. A self organization 4 of the purple membranes takes place in an oriented manner on the gold surface. Purple membranes with a false orientation 5 are not bound to the surface.
Figure 6:
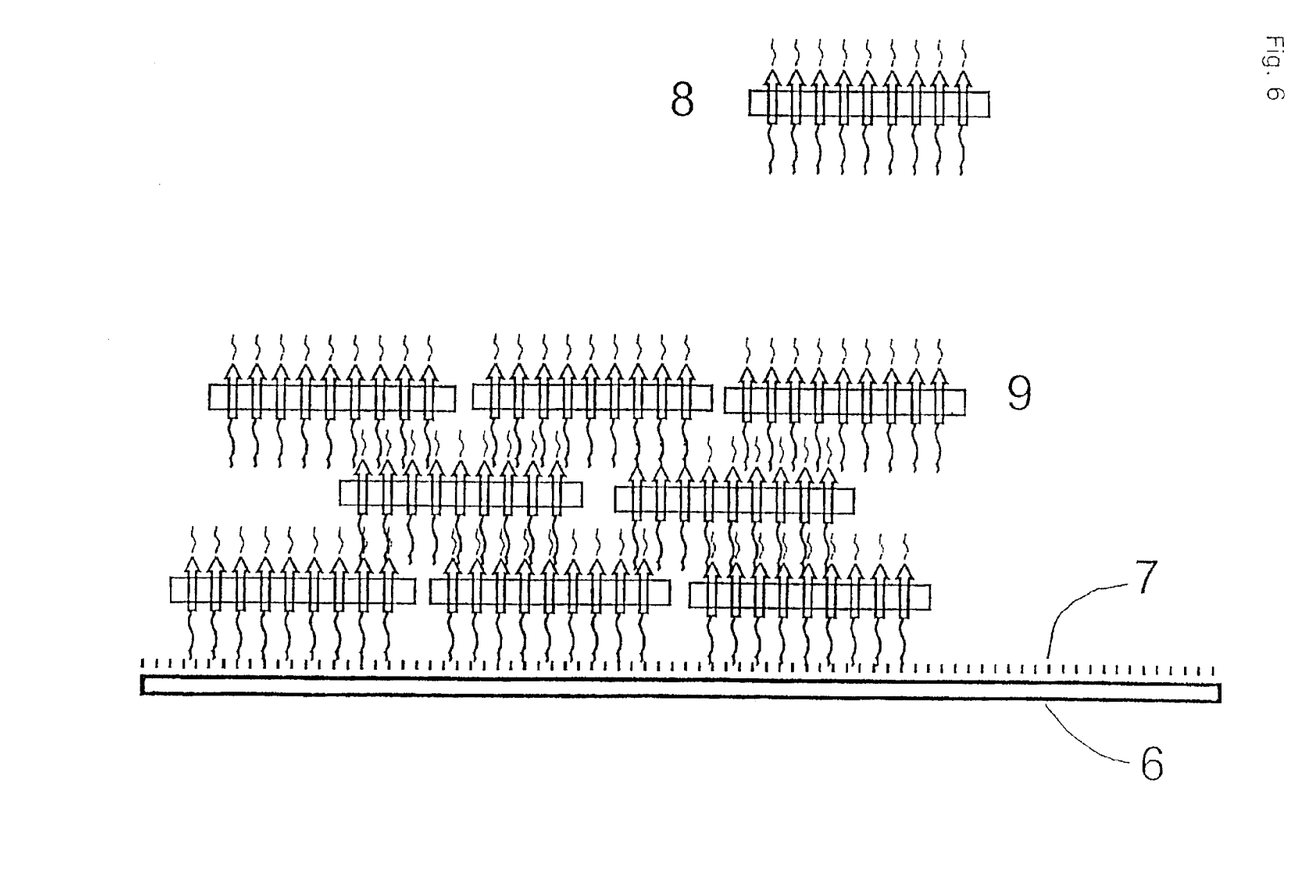

Reaction mixture as in 2). However, the reaction is stopped at a desired time point by briefly heating to 80° C. Cross-linked and non-cross-linked bacteriorhodopsin are then present in the reaction mixture. Any desired ratio of cross-linked to uncross-linked bacteriorhodopsin can be set by appropriate selection of the stop time (FIG. 2 and 3). The higher the degree of cross-linking, the more rigid the cross-linked bacteriorhodopsin becomes.

The red band in FIG. 3 represents BR-WT, the blue band represents BR-D2N. The lilac-coloured cross-linked product $BR-WT_x-BR-D2N_y$ is obtained by cross-linking.

Example 4

10% (w/v) of a gelatin solution (porcine skin gelatin) is mixed with the same volume of a BR solution (PM concentration 39.1 mg/ml) and with BTGase solution (12 U/ml) such that the amount of BTGase is comparable with the amount of the BR. The reaction solution is then incubated overnight at 37° C. The BR is then present in the reaction mixture bound in gelatin.

What is claimed is:

1. Process for the production of covalently cross-linked bacteriorhodopsin in the purple membrane form comprising reacting bacteriorhodopsin in the purple membrane form, as a substrate, with transglutaminase to become covalently cross-linked thereby.

2. Process as claimed in claim 1, wherein identical or different bacteriorhodopsins or bacteriorhodopsin variants are cross-linked with one another.

3. Process as claimed in claim 2, wherein the bacteriorhodopsin is selected from wild-type bacteriorhodopsin or/and bacteriorhodopsin variants.

4. Process as claimed in claim 2, wherein at least one bacteriorhodopsin variant is a membrane protein that is structurally related to bacteriorhodopsin.

5. Process as claimed in claim 2, wherein at least one bacteriorhodopsin variant has a modified amino acid sequence compared to the wild-type bacteriorhodopsin or/and in which retinal is replaced by a retinal-like molecule or/and is chemically modified or/and modified by enzymatic treatment.

6. Process as claimed in claim 5, wherein at least one bacteriorhodopsin variant contains only a single binding site for transglutaminase.

7. Process as claimed in claim 5, wherein at least one bacteriorhodopsin variant contains two binding sites for transglutaminase which are not on the same side of the membrane.

8. Process as claimed in claim 2, wherein the cross-linking reaction is stopped by heating to 80° C. or above.

9. Process as claimed in claim 1, wherein a bacterial transglutaminase is used.

10. Process as claimed in claim 2, wherein a transglutaminase is used which is active without a cofactor.

11. Process as claimed in claim 2, wherein the bacteriorhodopsin is cross-linked with a polymer, a surface or/and an auxiliary substance.

12. Process as claimed in claim 2, wherein the membrane protein is halorhodopsin or/and sensorrhodopsin in a membrane-bound form.

13. Process as claimed in claim 11, wherein the auxiliary substance is selected from the group consisting of dyes, fluorochromes, lipids, peptides, nucleic acids, synthetic oligomers and polymers, proteins, lectins, polysaccharides and conductive molecules.

14. A linker-free, covalently cross-linked bacteriorhodopsin made by the process of claim 1.

15. Process for a photoelectric application, comprising using the linker-free, covalently cross-linked bacteriorhodopsin as claimed in claim 14 in a photoelectric application.

16. Process for three-dimensional data storage, comprising using the linker-free, covalently cross-linked bacteriorhodopsin as claimed in claim 14 in three-dimensional data storage.

* * * * *

UNITED STATES PATENT AND TRADEMARK OFFICE
CERTIFICATE OF CORRECTION

PATENT NO. : 6,927,050 B1
DATED : August 9, 2005
INVENTOR(S) : Norbert Hampp et al.

It is certified that error appears in the above-identified patent and that said Letters Patent is hereby corrected as shown below:

Title page,
Item [75], Inventors, delete "Ame" and insert -- Arne --.

Signed and Sealed this

Eleventh Day of October, 2005

JON W. DUDAS
*Director of the United States Patent and Trademark Office*